United States Patent [19]
Di Cesare

[11] Patent Number: 5,423,766
[45] Date of Patent: Jun. 13, 1995

[54] SAFETY SHIELD HAVING SPRING TETHER

[75] Inventor: Paul Di Cesare, Norwalk, Conn.

[73] Assignee: Becton, Dickinson and Company, Franklin Lakes, N.J.

[21] Appl. No.: 296,575

[22] Filed: Aug. 26, 1994

[51] Int. Cl.$^6$ .............................................. A61M 5/32
[52] U.S. Cl. .................................. 604/192; 604/198; 604/263
[58] Field of Search ............... 604/192, 198, 187, 110, 604/263

[56] References Cited

U.S. PATENT DOCUMENTS

| | | | |
|---|---|---|---|
| 5,051,109 | 9/1991 | Simon | 604/263 |
| 5,242,417 | 9/1993 | Paudler | 604/192 |
| 5,246,427 | 9/1993 | Sturman et al. | 604/198 X |
| 5,344,408 | 9/1994 | Partika | 604/192 |
| 5,348,544 | 9/1994 | Sweeney et al. | 604/192 |

*Primary Examiner*—John D. Yasko
*Attorney, Agent, or Firm*—John L. Voellmicke

[57] ABSTRACT

A safety shield is provided for an elongate needle cannula having a proximal end and a sharply pointed distal tip. The safety shield includes an anchor fixedly disposed near the proximal end of the needle cannula. The safety shield further includes a tip guard that is slidably movable along the needle cannula from a proximal position near the anchor to a distal position where the tip guard protectively surrounds the distal tip of the needle cannula. An elongate spring tether formed from a resiliently deflectable material has a proximal end connected to the anchor and a distal end connected to the tip guard. The spring tether is deflected into a loop about an axis extending orthogonal to the needle cannula when the tip guard is in the proximal position. The spring tether has a length which permits the tip guard to slide into its distal position without sliding completely of the distal end of the needle cannula. Resiliency of the spring tether keeps the tip guard in its proximal position. However, after sufficient manually generated movement of the tip guard in a distal direction, the resiliency of the spring tether will propel the tip guard into its distal position for safely shielding the tip of the needle cannula.

14 Claims, 6 Drawing Sheets

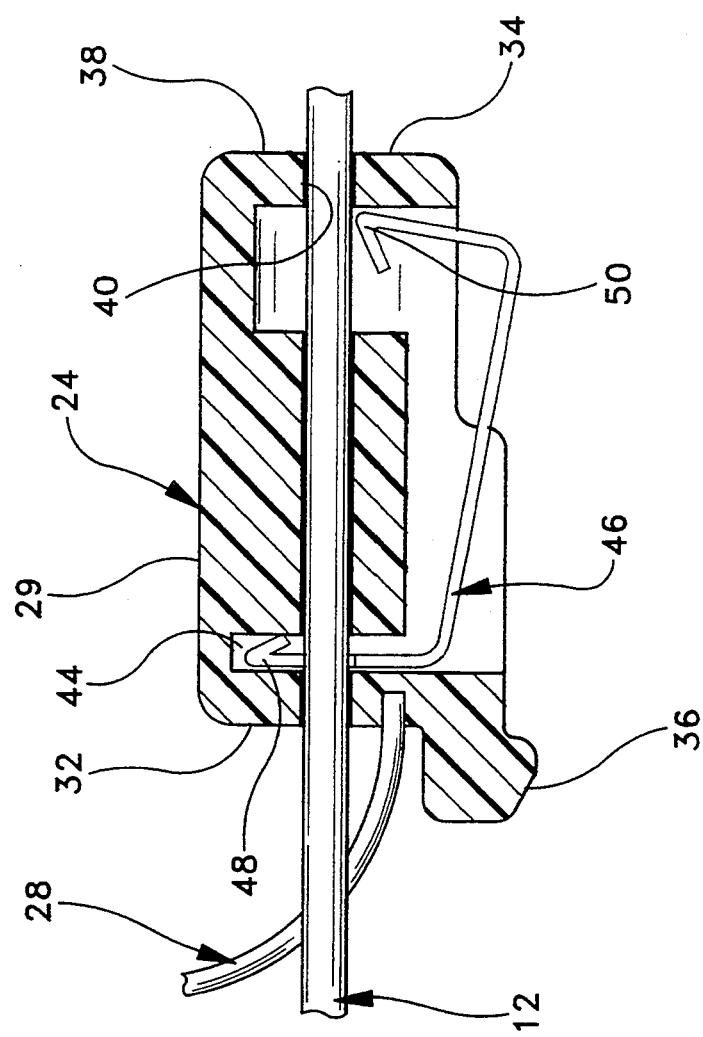
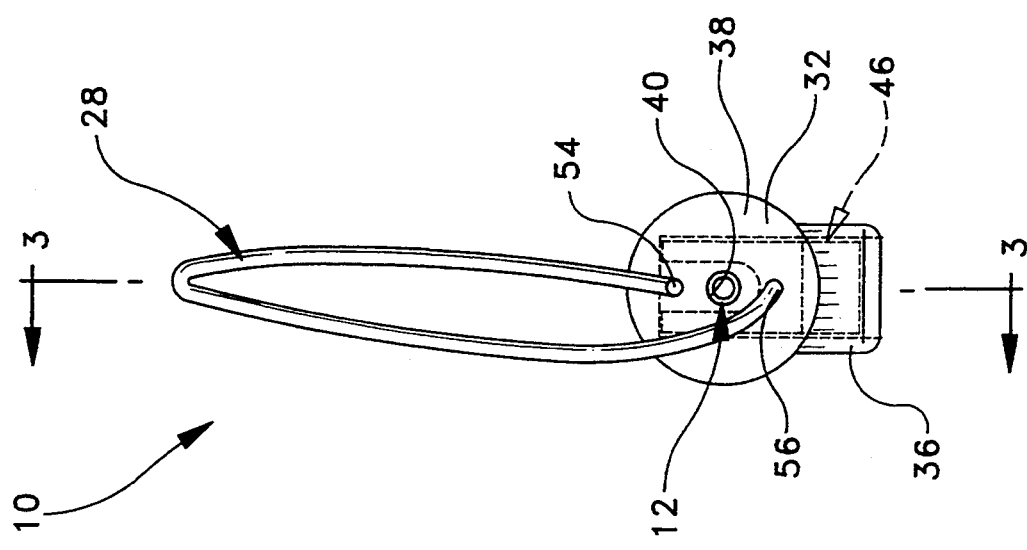

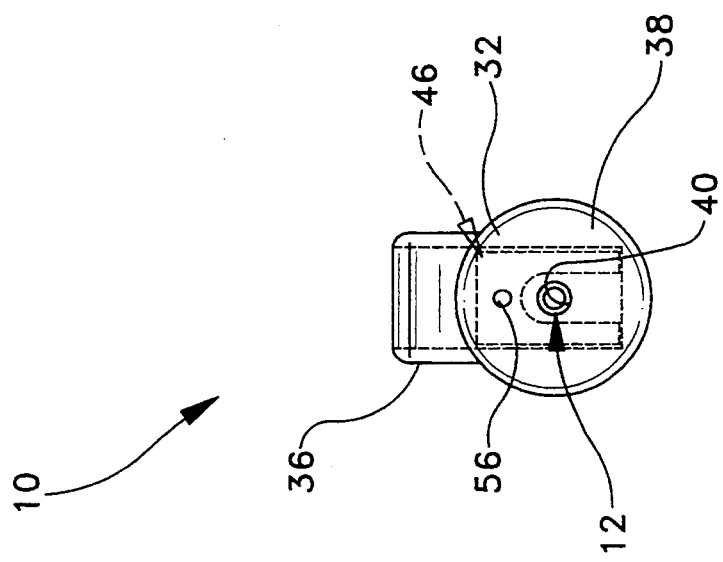
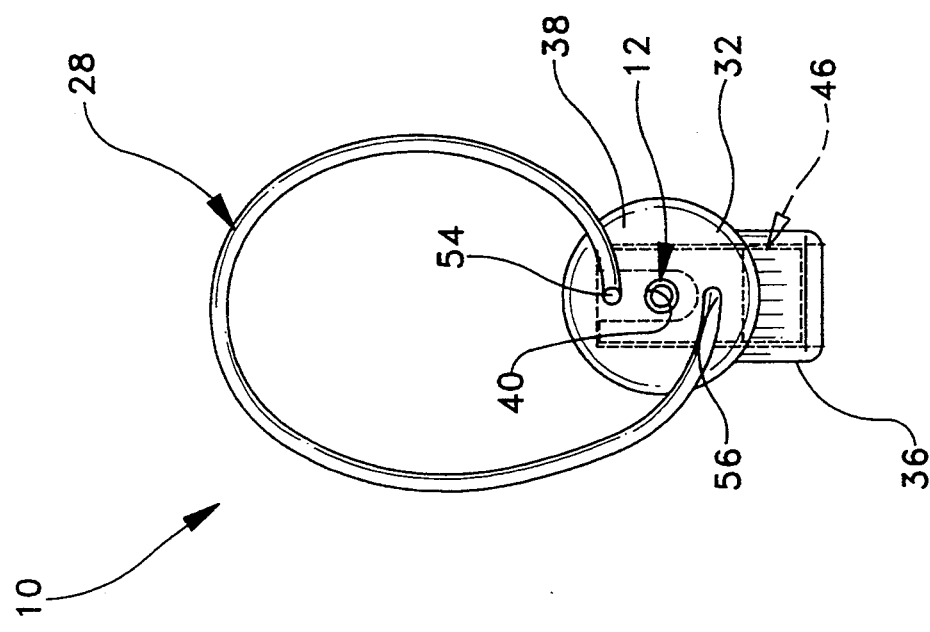

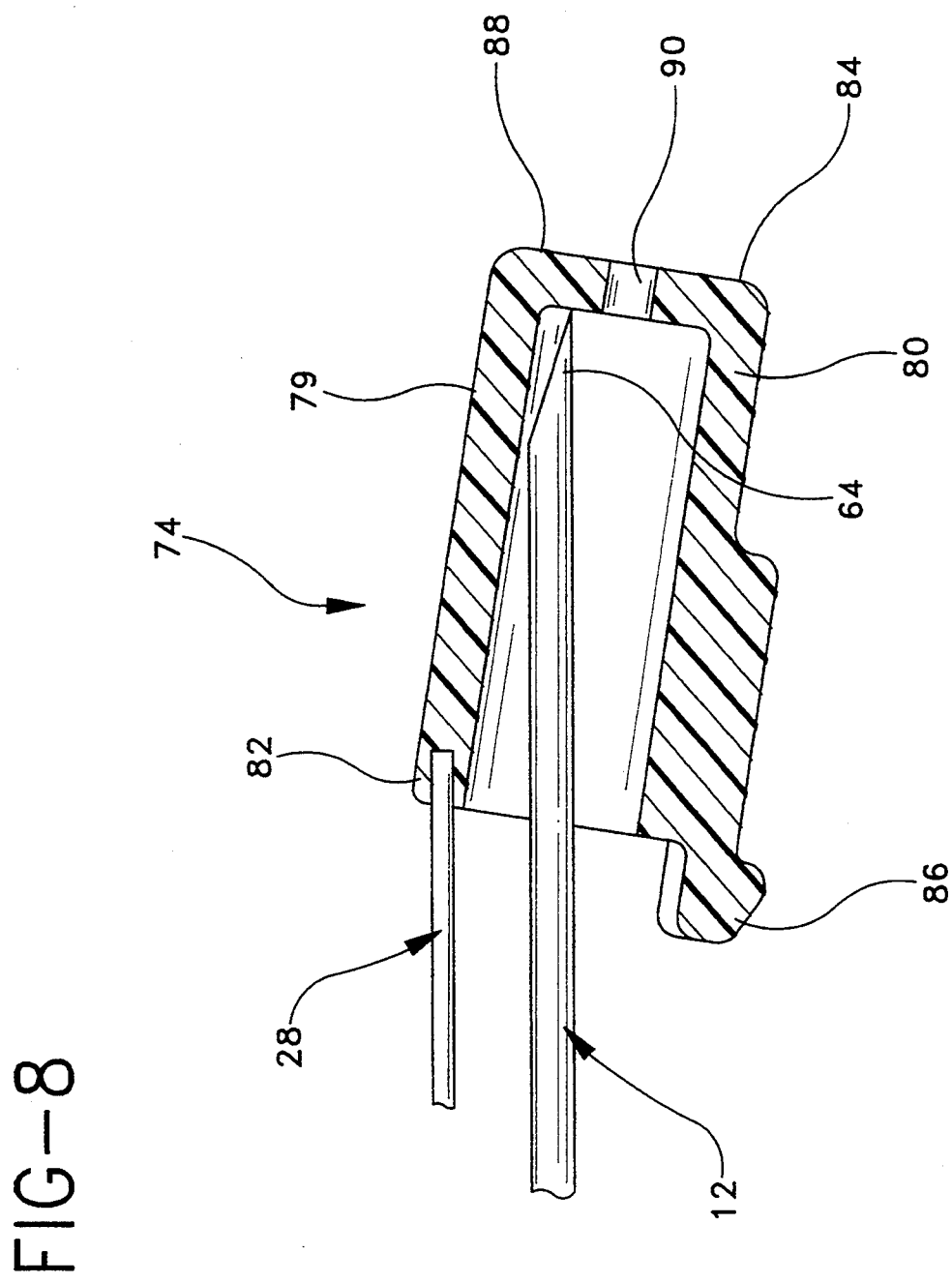

SAFETY SHIELD HAVING SPRING TETHER

BACKGROUND OF THE INVENTION

1. Field of the Invention

The subject invention relates to single-handedly actuatable safety shields for needles to prevent accidental needle sticks.

2. Description of the Prior Art.

Accidental sticks with a used medical implement can transmit disease. Consequently many prior art hypodermic needles, blood collection needles, catheter needles and other sharply pointed medical implements are provided with a safety shield. The safety shield is intended to be placed over the sharply pointed tip of the medical implement immediately after removing the medical implement from the patient.

Some prior art safety shields define a rigid cap that can be telescoped in a proximal direction over the point of the needle cannula or other such medical implement. This re-shielding procedure requires the health care worker to hold the pointed medical implement in one hand and the shield in the other. The hands are then moved toward one another to effect the shielding. However, a misalignment during the shielding procedure could cause the accidental stick that the shield is intended to avoid. Additionally, this prior art shield presupposes that the health care worker will have two free hands to complete the shielding and that the shield will be readily available when the needle cannula or other such pointed implement is removed from the patient. In fact, many medial procedures require the health care worker to apply pressure to the penetration site immediately after the needle has been removed. Thus, the health care worker will apply pressure with one hand while manipulating the medical implement with the other hand. The unshielded needle may be placed on a nearby surface for shielding at a later time. This re-shielding easily can be overlooked as the health care worker attends to other needs of the patient. Additionally, the needle shield easily can be moved or misplaced between the initial unshielding and the intended reshielding.

Other prior art needle shields remain attached to the medical implement to avoid loss. The attachment may be a simple tether extending between the above described shield and the medical implement. Upon completion of a medical procedure, the health care worker will perform the two-handed telescoping of the tethered shield in a proximal direction over the point of the needle. This prior art shield avoids problems associated with loss. However, shielding cannot be completed until the health care worker has two free hands and the above-described potential exists for an accidental needle stick during the two-handed shielding procedure.

Still other prior art needle shields are constructed to enable single handed shielding. For example, some prior art shields are hingedly connected to the medical implement at or near the base of the needle. The shield is a rigid elongate structure, larger than the needle cannula, and open on one side to accept the needle. The shield is rotated away from the needle cannula while the medical implement is being used. The health care worker then uses one finger of the hand holding the medical implement to rotate the shield about the hinge and into a position where the needle cannula is partly surrounded. A variation of this basic design is disclosed in U.S. Pat. No. 5,242,417 which shows an over-center hinge connecting a shield to a medical implement. The over-center hinge is stably maintained in a rotational position that enables access to the needle cannula. After use, the shield is rotated toward the needle cannula. Initial rotational movement must overcome biasing forces exerted by the hinge. However, after sufficient rotational movement, the internal resiliency of the hinge urges the shield toward the needle cannula. The prior art hinged shields provide several efficiencies. However, the shield can sometimes interfere with convenient use of the medical implement and can block clear vision of the penetration site.

Prior art medical implements also include a needle shield that is telescoped over portions of the medical implement. These prior art shields are maintained in a proximal position over the medical implement prior to and during use. The shield then can be telescoped in a distal direction to safely surround the used needle cannula. Prior an shields of this type generally reduce the potential for accidental needle sticks during a shielding operation. However, these prior art shields can add significantly to the size, weight and cost of the medical implement. Additionally, most prior art shields of this type require two-handed activation of the shield. As noted above, two hands may not be available to the health care worker immediately after using the medical implement. Thus, the used medical implement may be kept in an unshielded condition. Prior art telescoping shields have been used with coil springs that are concentric with the needle cannula and that extend between the medical implement and the shield. A latch on the medical implement may keep the coil spring in a compressed condition prior to and during use of the medical implement. The latch may be released by a finger of the hand holding the medical implement to propel the shield distally and into a shielding disposition around to the needle cannula. Coil springs overcome the problem of two-handed activation. However, they further add to the size, weight and cost of the implement. Furthermore, the locks for holding further add to the complexity of the apparatus. These small plastic latches can possibly fail by either misfiring under the force of the spring or not releasing the spring at all.

SUMMARY OF THE INVENTION

The subject invention is directed to a single-handedly activatable safety shield for a needle cannula that may be used with a hypodermic syringe, a blood collection device, a catheter needle, or other medical implement. The needle cannula includes a sharply pointed distal tip and a proximal end that can be placed in communication with the medical implement, such as a hypodermic syringe.

The safety shield of the subject invention includes a guard that is slidably mounted on the needle cannula for movement between a proximal position where the distal tip of the needle cannula is readily accessible and a distal position where the sharply pointed distal tip of the needle cannula is safely enclosed. The guard may be plastic, but may include a metallic member securely engaged or retained therein. The metallic member may be biased against the needle cannula for sliding movement with the cap along the needle cannula. However, after sufficient movement of the guard distally along the needle cannula, the metallic member will pass the distal tip of the needle cannula. The metallic member will then be biased into a position for protectively coveting the distal tip of the needle cannula and preventing a return or proximal movement of the guard.

The safety shield of the subject invention further includes an elongate spring tether. The spring tether may be formed from a spring wire, fiber glass, plastic or other material that exhibits flexibility, resiliency and adequate degrees of strength and dimensional stability as explained further herein. The spring tether includes opposed proximal and distal ends. The distal end of the spring tether is connected to or unitary with the above described guard of the safety shield. The proximal end of the spring tether is connected to or unitary with an anchor remote from the distal end of the needle cannula. For example, the anchor may be connected to or be unitary with the hub of the needle cannula that enables connection of the needle cannula to a hypodermic syringe or other medical implement. The spring tether defines a length sufficient to enable the guard of the safety shield to protectively enclose the distal tip of the needle cannula without permitting the guard to travel distally beyond the needle cannula.

The resiliency of the spring tether causes the spring tether to loop into a single coil about an axis substantially orthogonal to the needle cannula when the guard is moved into its proximal position near the anchor. By substantially orthogonal it is meant that the axis crosses the longitudinal axis of the needle cannula rather than being in a substantially parallel relationship with the longitudinal axis of the needle cannula. In this position, the opposed proximal and distal ends of the spring tether are near one another and are substantially axially aligned. Importantly, the spring tether is stable in this looped condition with the guard of the safety shield being conveniently urged in a proximal direction by the resiliency of the spring tether. Although separate latches may be provided they are not required to keep the guard of the safety shield in the proximal position.

The spring tether of the safety shield is in its looped condition prior to and during use of the needle cannula, with the guard being stably maintained in its proximal position on the needle cannula. In this position the distal tip of the needle cannula is readily visible and accessible for use in its normal manner. Significantly, the spring tether is cross-sectionally very small, and hence provides virtually no visual obstruction. As a result the health care worker can readily observe the puncture site, the orientation of the bevel on the distal tip of the needle cannula, and the depth of injection.

After withdrawal of the needle cannula from the patient, the health are worker merely exerts a distally directed force on the guard of the safety shield. This force conveniently can be exerted with a finger of the hand in which the medical implement is held by the health care worker. Initial forces exerted on the guard must overcome the biasing forces that maintain the resilient spring tether stably in its looped condition. However, after the spring tether uncoils beyond its point of stability, the inherent resiliency of the spring tether will propel the guard distally along the needle cannula until the spring tether reaches a fully extended and stable condition. The guard attached to the distal end of the spring tether will protectively enclose the distal tip of the needle cannula when the spring tether reaches the fully extended position. As noted above, the guard may include a metallic member that is biased against the needle cannula to slide therealong. When the spring tether is urged into its stable linear condition, the metallic member within the guard will have slid distally beyond the tip of the needle cannula and will biasingly urge itself over the tip of the needle cannula. Thus, the metallic member prevents a return proximal movement of the guard that could otherwise re-expose the tip of the used needle cannula. Conversely, the extended spring tether prevents the guard from moving distally beyond the needle cannula.

BRIEF DESCRIPTION OF THE DRAWINGS

FIG. 2 is a cross-sectional view taken along line 2—2 in FIG. 1.

FIG. 3 is a cross-sectional view taken along line 3—3 in FIG. 2.

FIG. 5 is a cross-sectional view taken along line 5—5 in FIG. 4.

FIG. 7 is a cross-sectional view taken along line 7—7 in FIG. 1.

FIG. 8 is another embodiment of the spring tether and tip guard.

DETAILED DESCRIPTION

Figure 1:
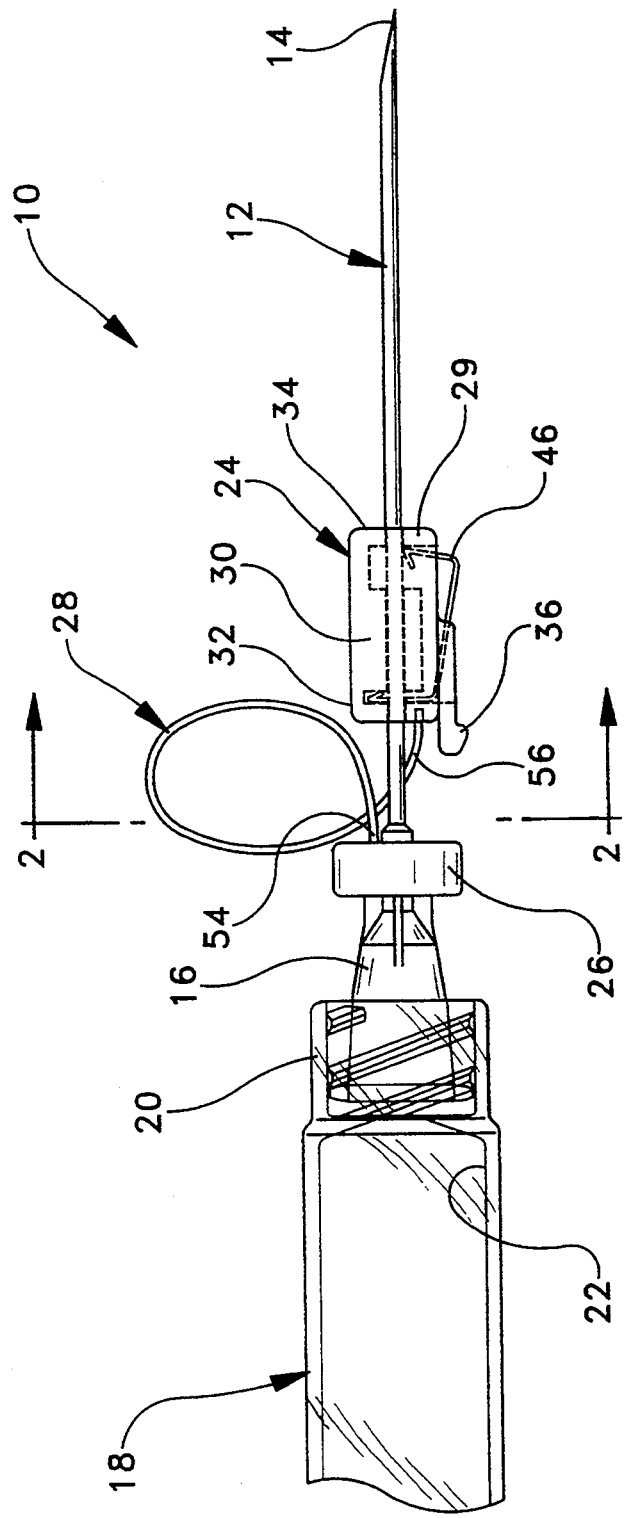
FIG. 1 is a side elevational view showing the needle shield disposed in a first stable position on a needle cannula for permitting use of the needle cannula.
Figure 4:
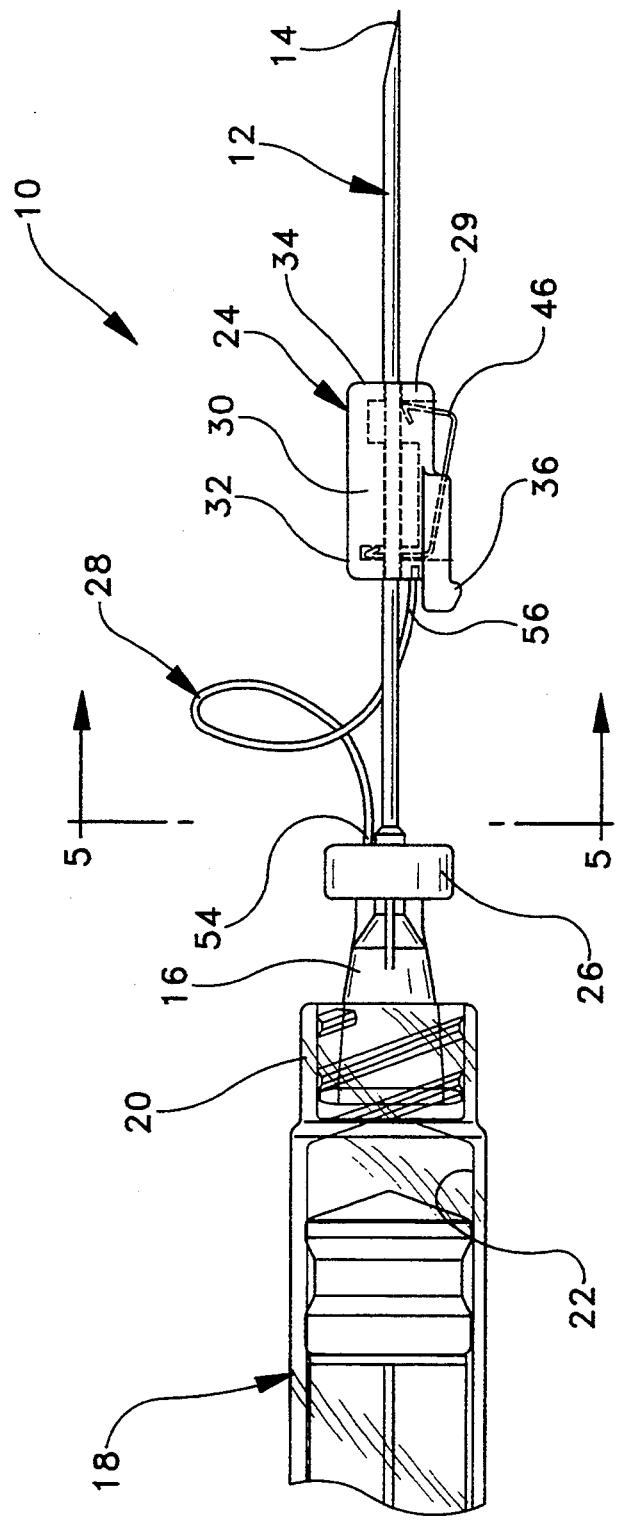
FIG. 4 is a side elevational view similar to FIG. 1, showing the needle shield in an intermediate and unstable position on the needle cannula.

A needle shield in accordance with the subject invention is identified generally by the numeral 10 in FIGS. 1-7. Needle shield 10 is used with a needle cannula 12 which has a sharply pointed distal tip 14 and a proximal end joined to a needle hub 16. Needle cannula 12 is used with a hypodermic syringe 18 which has a luer collar 20 defining a distal end thereof. Hub 16 is threadedly engageable with luer collar 20 of hypodermic syringe 18 to place needle cannula in communication with a fluid receiving chamber 22 defined within hypodermic syringe 18.

Needle shield 10 includes a tip guard 24, an anchor 26 and a spring tether 28 extending therebetween. Guard 24 includes a cap 29 having a side wall 30 which is generally tubular in this embodiment. Cap 29 includes opposed proximal and distal ends 32 and 34 respectively. An actuating tab 36 extends proximally and slightly outwardly from distal end 32 of side wall 30 and is dimensioned for easy manipulation by a finger of a hand-holding hypodermic syringe 18. An end wall 38 extends transversely across distal end 34 and includes a needle receiving aperture 40 extending centrally therethrough.

Guard 24 further includes a spring lock 46 disposed therein. Spring lock is formed from a resilient puncture resistant material such as spring metal, and includes a bent mounting portion 48 that is frictionally embedded in receiving slot 44 of the guard. A needle engaging portion 50 that is biased against needle cannula 12. Guard 24 is axially movable such that needle engaging portion 50 of spring lock 46 and portions of end wall 38 adjacent aperture 40 slidably engage needle cannula 12.

Anchor 26 of needle shield 10 is rigidly fixed relative to needle cannula 12 at a location remote from distal tip 14. In the embodiment depicted herein, anchor 26 is plastic and is unitarily molded with needle hub 16. In other embodiments, however, anchor 26 may be adhered to needle cannula 12 and/or hub 16. Alternatively, anchor 26 may be a separate component locked to hub 16 or attached directly to the syringe barrel through the use of mechanical means, adhesives, welding or the like.

Figure 6:
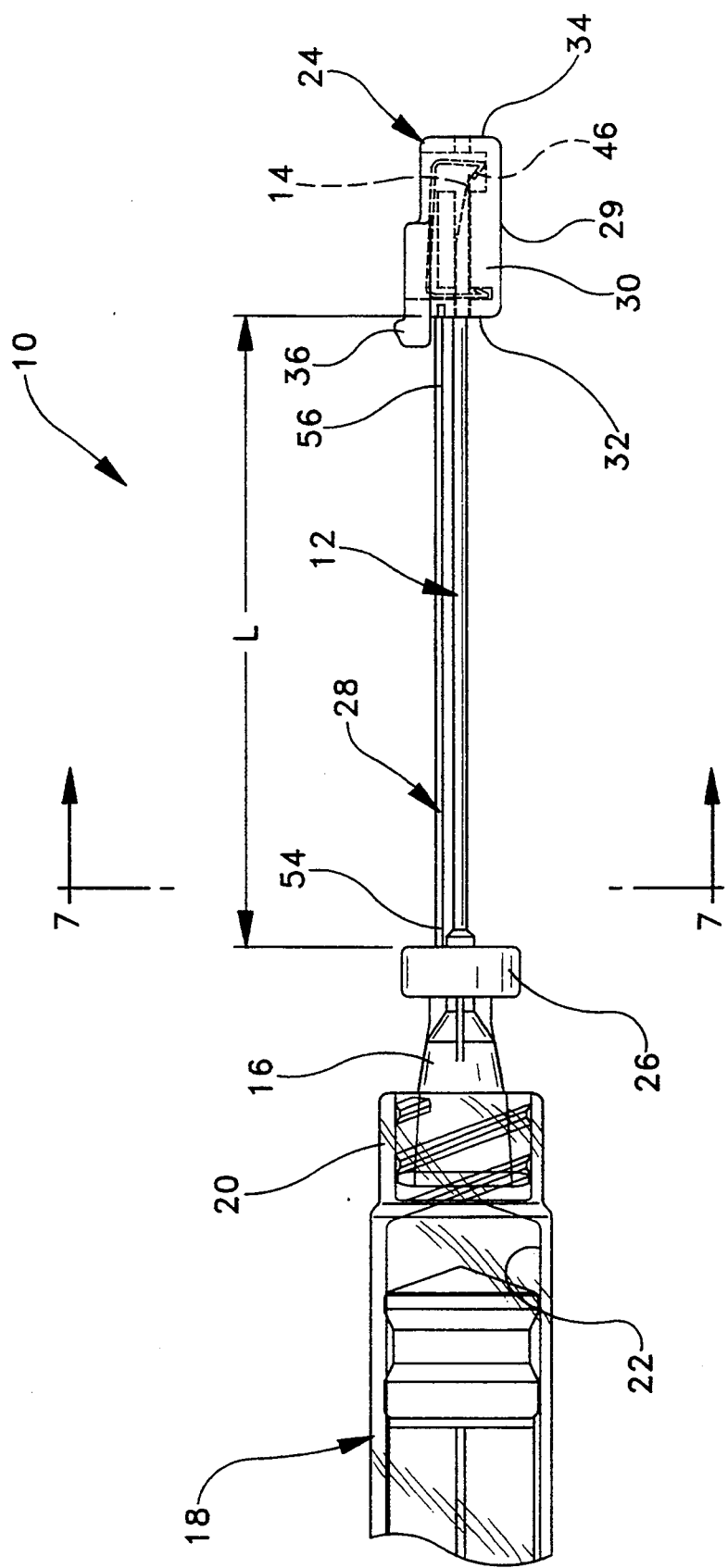
FIG. 6 is a side elevational view similar to FIGS. 1 and 4, showing the needle shield in a second stable condition which prevents use of the needle cannula.

Spring tether 28 includes a proximal end 54 connected to guard 24 and a distal end 56 connected to anchor 26. Spring tether 28 defines an exposed length "L" as shown in FIG. 6 which permits guard 24 to move distally over tip 14 of needle cannula 12. Spring tether 28 is formed from a material that exhibits resiliency, strength and dimensional stability such as fiber glass and metal spring wire with steel spring wire being preferred. More particularly, spring tether 28 is resiliently deflectable into a dynamically stable loop, as shown in FIG. 1, about an axis substantially orthogonal to needle cannula 12. In this looped condition, regions of looping spring tether 28 adjacent proximal and distal ends 54 and 56 are preferably substantially adjacent and substantially parallel to the longitudinal axis of needle cannula 12. Spring tether 28 will try to resiliently return to a substantially linear alignment, with proximal end 54 being resiliently urged in a distal direction and toward needle cannula 12, and distal end 56 being resiliently urged in a proximal direction and toward needle cannula 12. However, guard 24 and anchor 26 efficiently prevent spring tether 28 from springing open. Hence, the resiliency of spring tether 28 urges guard 24 proximally and toward anchor 26 to define a stable condition which permits use of needle cannula 12. Also, when the guard is in the retracted position the forces exerted on the anchor and the guard by the spring tether are primarily directed perpendicularly to the axis of the needle which increases the frictional forces between the cannula and the tip guard to further stabilize the needle shield.

Spring tether 28 is initially placed in the looped condition shown in FIGS. 1 and 2 by urging guard 24 proximally and into a position substantially adjacent or near anchor 26. A removable outer needle shield (not shown) may be telescoped over needle cannula 12 to prevent against accidental needle sticks prior to use of needle cannula 12. The outer needle shield may includes a longitudinally extending slot for receiving spring tether 28, and may be frictionally mounted to anchor 26, needle hub 16 or luer collar 20. The outer shield may be removed in the conventional manner to enable use of needle cannula 12 and hypodermic syringe 18. The thin spring tether 28 will provide virtually no physical or visual obstruction. Hence, a health care worker can accurately orient the bevel at tip 14 of needle cannula 12 and can target a precise location on the patient and can visually gauge the depth of injection.

After withdrawal of needle cannula 12 from the patient, the health care worker exerts a distally directed force on actuating tab 36 of guard 24. This distally directed force causes guard 24 to move distally along needle cannula 12. This initial distal movement of guard 24 must overcome the resiliency of spring tether 28. However, resistance of spring tether 28 is small compared to the forced exerted by a finger of the health care worker. Resiliency of spring tether 28 prevents the spring tether from collapsing onto itself in response to distal forces exerted by the health care worker on guard 24. Rather, spring tether 28 will effectively be rotated from the FIG. 2 orientation where the axis of spring tether 28 is substantially orthogonal to needle cannula 12, into the FIGS. 4 and 5 orientation where the axis of the loop becomes more aligned to longitudinal axis of the needle cannula 12. The component of the resilient forces that initially urged guard 24 in a proximal direction become less as guard 24 moves distally and as spring tether 28 gradually opens and rotates. At approximately the position depicted in FIGS. 4 and 5, the inherent resiliency of spring tether 28 will begin to propel guard 24 distally. These distal forces will continue until spring tether 28 achieves the linear alignment depicted in FIGS. 6 and 7.

As noted above, length "L" of spring tether 28 is selected to position guard 24 over distal tip 14 of needle cannula 12 when spring tether 28 is in the linear alignment shown in FIG. 6. Additionally, in this position, needle engaging portion 50 of spring lock 46 will have passed distally beyond tip 14 of needle cannula 12. The resiliency of spring lock 46 will urge needle engaging portion 50 thereof over distal tip 14 as shown in FIG. 6 and 7. In this position, spring tether 28 prevents further distal movement of guard 24 while spring lock 46 prevents a return proximal movement of guard 26. Thus, distal tip 14 of needle cannula 12 is safely protected within guard 24 to prevent accidental needle sticks or intentional reuse.

FIG. 8 illustrates another embodiment of the needle shield of the present invention. In this embodiment the spring tether performs in substantially the same way as in the embodiment of FIGS. 1-7. However, in the embodiment of FIG. 8 the means for preventing the tip guard from returning to the retracted position after it is in the needle protecting position is different. Specifically, the embodiment of FIG. 8 includes spring tether 28 and tip guard 74. Tip guard 74 includes proximal end 82, distal end 84 and end wall 88 at the distal end running across the distal end of the tip guard. End wall 88 includes needle receiving aperture 90 which is generally aligned with tubular side wall 80 of the tip guard. Activating tab 86 is provided for application of digital pressure on the tip guard. The assembly of resilient spring tether 28 and tip guard 74 is made, so that at rest, the axis of needle receiving aperture 90 is at an angle to the longitudinal axis of the spring tether 28. However, when the tip guard is in its retracted proximal position on the needle cannula, the needle cannula forces the alignment of the axis of the needle receiving aperture in the tip guard to align with the longitudinal axis of the needle cannula. However, when the tip guard is fully extended in the needle covering position it will assume the orientation of its assembly as shown in FIG. 8. The misalignment causes the needle tip 64 to move out of alignment with needle receiving aperture 90 and to contact the inside of end wall 88. Proximally directed force will cause needle tip 64 to embed itself into end wall 88, thus preventing re-exposure of the needle cannula.

The invention has been described with respect to a limited number of embodiments. However, it is to be understood that variations can be provided. In particular, spring tether 28 has been depicted as being unitary with both guard 24 and anchor 26. However, a separate spring tether may be securely connected to a cap and anchor. This separate spring tether may be formed from any material exhibiting appropriate strength, resiliency and dimensional stability, such as a metallic spring wire. Additionally, spring lock 46 may not be required for some embodiments. Finally, as noted above, needle shield 28 may be used with medical implements and needle configurations for other than hypodermic syringes, such as the dual pointed needle used to transfer blood from a patient's vein and an evacuated receptacle.

What is claimed is:

1. A safety shield comprising an elongate needle cannula having a proximal end and an opposed distal tip;
an anchor disposed substantially adjacent said proximal end of said needle cannula;
a guard slidably movable along said needle cannula from a proximal position substantially adjacent said anchor to a distal position where said tip guard protectively encloses said distal tip of said needle cannula; and
an elongate spring tether formed from a resiliently deflectable material, said spring tether having a proximal end connected to said anchor and a distal end connected to said guard, said spring tether being deflectable into a loop and about an axis substantially orthogonal to said needle cannula when said guard is in said proximal position, said spring tether defining a length for permitting said guard to slidably move into said distal position while preventing complete separation of said guard from said needle cannula, whereby said resiliency of said spring tether biases said guard proximally when said guard is near said proximal position, and whereby said resiliency of said spring tether propels said guard to said distal position after an initial distal movement of said guard toward said distal position.

2. The safety shield of claim 1, wherein said anchor, said guard and said spring tether are formed from a plastic material.

3. The safety shield of claim 2, wherein said anchor, said guard and said spring tether are unitary with one another.

4. The safety shield of claim 1, wherein said spring tether is formed from fiber glass.

5. The safety shield of claim 1, wherein said spring tether is formed from a resilient metallic wire.

6. The safety shield of claim 1, wherein said guard includes an actuator tab projecting generally transversely away from said needle cannula for manually urging said guard distally away from said proximal position and against said biasing forces of said spring tether.

7. The safety shield of claim 1, wherein said needle cannula includes a mounting hub affixed to said proximal end of said needle cannula, said anchor being securely connected to said needle hub.

8. The safety shield of claim 7, wherein said anchor is unitary with said hub.

9. The safety shield of claim 1, wherein said guard includes a spring lock disposed therein, said spring lock being biased to contact said needle cannula as said guard moves from said proximal position toward said distal position, said spring lock being configured for biasingly engaging over said distal tip of said needle cannula when said guard is in said distal position to prevent proximal motion of said guard.

10. The safety shield of claim 9, wherein said guard defines a generally cylindrical cap surrounding said needle cannula, said spring lock being lockingly retained within said cap of said guard.

11. The safety shield of claim 1, wherein said spring tether defines a length for preventing said guard from sliding distally beyond said distal tip of said needle cannula.

12. The safety shield of claim 1 further including an elongate syringe barrel having a distal end, a proximal end and a sidewall therebetween, said proximal end of said needle connected to said distal end of said barrel.

13. A safety needle shield assembly comprising: an elongate needle cannula having a distal tip and an opposed proximal end securely engaged to a needle hub;
a guard slidably movable along said needle cannula from a proximal position substantially adjacent said hub to a position where said guard surrounds said distal tip;
an elongate spring tether formed from a resiliently deflectable material, said spring tether having a proximal end connected to said hub and a distal end connected to said guard, said spring tether being deflectable into a loop generated about an axis substantially orthogonal to said needle cannula when said guard is in said proximal position, said spring tether being operative to propel said guard into said distal position after an initial manually generated distally directed movement of said guard along said needle cannula.

14. The safety shield of claim 13, wherein said guard includes a spring lock resiliently connected thereto for engaging said tip of said needle cannula when said guard is in said distal position.

* * * * *